United States Patent [19]

Arnon et al.

[11] Patent Number: 4,474,757
[45] Date of Patent: Oct. 2, 1984

[54] SYNTHETIC VACCINE AND PROCESS FOR PRODUCING SAME

[75] Inventors: Ruth Arnon, Rehovot; Michal Shapira, Ness Ziona; Gunhild Müller, Rehovot, all of Israel

[73] Assignee: Yeda Research & Development Company Ltd., Rehovot, Israel

[21] Appl. No.: 335,574

[22] Filed: Dec. 29, 1981

[30] Foreign Application Priority Data

Jan. 13, 1981 [IL] Israel ................................... 61904

[51] Int. Cl.³ .................... A61K 39/00; A61K 37/02; C07C 103/52; C07G 7/00
[52] U.S. Cl. ....................................... 424/88; 424/89; 424/177; 260/112 R; 260/112.5 R
[58] Field of Search ........................... 424/88, 177, 89; 260/112.5 R, 112 R

[56] References Cited

PUBLICATIONS

Sela, M. et al., "Antiviral Antibodies Obtained with Aqueous Solution of a Synthetic Antigen", *New Developments with Human & Vet. Vaccines* pp. 315–323 (1980).
Arnon, R. "Synthetic Vaccines—A Dream or Reality" *Eur. J. Biochem.* 31, 534–540 (1972).
Arnon, R. et al., "Antiviral Response Elicited by a Completely Synthetic Antigen with Built-in Adjuvanticity" *Proc. Natl. Sci. U.S.A.* vol. 77, No. 11, pp. 6769–6772 (1980).
Muller, G. M. et al., "Anti-Influenza Response Achieved by Immunization with a Synthetic Conjugate", *Proc. Natl. Acad. Sci. USA*, vol. 79, pp. 569–573 (1982).
Laver, W. G. et al., "Amino Acid Sequence Changes in the Haemagglutinin of A/Hong Kong (H3N2) Influenza Virus During Period 1968–1977" *McMillan Journals Ltd.* (1980) pp. 454–457.
Jackson, D. C. et al., "Immunogenicity of Fragments Isolated from the Hemagglutinin of A/Memphis/72", *The Journal of Immunology*, vol. 123, No. 6, pp. 2610–2617 (1979).
Lerner, R. A., "Synthetic Vaccines" *Scientific American*, pp. 66–74 (1983).
Walter et al., *Proc. Natl. Acad. Sci. USA*, vol. 77, No. 9, pp. 5197–5200, Sep. 1980.
Sutcliffe et al., *Nature*, vol. 287, pp. 801–805, Oct. 30, 1980.
Arnon et al., *Proc. Natl. Acad. Sci. USA*, vol. 68 No. 7, pp. 1450–1455 (1971).
Langbeheim et al., *Proc. Natl. Acad. Sci. USA*, vol. 73 No. 12, pp. 4636–4640 (1976).
Davis et al., *Gene*, vol. 10, pp. 205–218 (1980).

*Primary Examiner*—Blondel Hazel
*Attorney, Agent, or Firm*—Browdy and Neimark

[57] ABSTRACT

There is provided a synthetic vaccine against influenza virus infections consisting of a synthetic peptide corresponding to a relevant antigenic fragment of the virus, which fragment is attached to a suitable carrier, such as a macromolecule. Effective vaccinations against a plurality of strains can be obtained when the antigenic fragment is one common to such strains. Such synthetic vaccines are produced by synthesizing peptides corresponding to such relevant antigenic fragments and coupling same to a suitable carrier, such as a macromolecule. There is also provided a process for the vaccination of mammals against influenza which comprises applying to said mammals an effective quantity of a vaccine according to the invention.

13 Claims, 3 Drawing Figures

A = RABBIT — HAI(18) TOXOID
B+E = HAI(18) TOXOID
C+D = TOXOID

DOUBLE DIFFUSION IN AGAR GEL

RIA WITH PEPTIDE

| SERA | ANTIGEN | |
|---|---|---|
| ANTI HA$_I$(18)-TOXOID | HA$_I$(18) | (×——×) |
| ANTI HA$_I$(18)-TOXOID | NO Ag | (○——○) |
| PRE-IMMUNE SERUM | HA$_I$(18) | (△——△) |

HEMAGGLUTINATION INHIBITION TEST

4 HAU OF A/Vic/1/75 ANTIGEN WERE INCUBATED WITH X2 SERIAL DILUTIONS OF THE IgG FRACTION OF ANTI $HA_1(18)$-TOXOID.
CHICKEN ERYTHROCYTES WERE ADDED TO A FINAL CONCENTRATION OF 0.25%. RESULTS WERE READ STARTING AFTER 30'.

SYNTHETIC VACCINE AND PROCESS FOR PRODUCING SAME

FIELD OF THE INVENTION

The present invention relates to novel synthetic vaccines and to a process for the production of same. A specific embodiment of the invention relates to a novel synthetic vaccine against influenza and to a process for the production of same. The invention further relates to the synthesis of relevant antigenic fragments of this virus, to the thus obtained products, to the attachment of same to macromolecular carriers, to such conjugates, and to the use of same as vaccines.

BACKGROUND OF THE INVENTION

The invention is illustrated in the following with reference to the production of a synthetic vaccine against influenza. It ought to be understood that the invention is not restricted to this specific embodiment, and that the principles of preparation of synthetic antigenic fragments can be applied to other viruses, and that such products can be the basis for the production of vaccines against other diseases.

Influenza virus appears as three subtypes, A, B and C, of which subtype A comprises the major antigenic variants that are associated with pandemics. This subtype is capable of changing its antigenic identity so remarkably that the specific immunity established in response to infection or vaccination by a particular strain may give little or no protection against viruses which subsequently arise. Because of these variants influenza continues to be a major epidemic disease in man.

Presently existing vaccines against influenza consist of either live, attenuated virus, or killed virus vaccines. The live vaccines are more potent than the killed ones, but are not considered safe enough, and the duration of the protection provided by either vaccine is rather short.

The two principal antigenic components of the virus are: (1) The neuraminidase which is common to many influenza strains and antibodies against it are almost non-neutralizing and non-protective, and (2) the hemagglutinin (HA), which undergoes gradual changes (drifts), which is a strong immunogen and is responsible for the serological specifity of the different viral strains. Antibodies against the HA render the immune host less susceptible to infection with a virus containing the same hemagglutinin. Complexes of the hemagglutinin and the neuraminidase have also been utilized as potential vaccines, but these "subunit vaccines" proved to be poorly immunogenic in unprimed animals and in man.

The HA is a molecule of 75,000 to 80,000 dalton, and a CNBr cleavage fragment of it was found to be responsible for the immunological activity of the intact protein and it was found to be able to elicit antibodies which inhibit its hemagglutinin activity. A non-identified 16-amino acid residue tryptic peptide of the hemagglutinin was also reported as possessing antigenic specificity. Neither of these fragments nor any other similar natural or synthetic material has been used for eliciting an in vivo protective effect.

In other systems short synthetic peptides corresponding to fragments of particular proteins have been shown to carry antigenic properties of the intact protein. Thus, synthetic antigens have been used for provoking antibodies against lysozyme or carcinoembryonic antigen (CEA). The same approach was employed for eliciting anti-viral response: A synthetic 20-amino acid residue peptide corresponding to a fragment of the coat protein of the MS-2 coliphage has been synthesized and attached to a synthetic carrier. This conjugate, when injected in complete Freund's adjuvant, elicited in rabbits and guinea pigs antibodies capable of neutralizing the viability of the phage.

SUMMARY OF THE INVENTION

The present invention relates to a novel synthetic anti-influenza vaccine and to a process for the production thereof. The novel process comprises synthesizing the relevant antigenic fragment of the virus, attaching same to a suitable macromolecular carrier and using the thus obtained compound as vaccine. More particularly, a preferred embodiment of the invention relates to a novel synthetic vaccine against influenza and to the production thereof. The first step is the synthesis of a synthetic peptide corresponding to an antigenic fragment of influenza hemagglutinin. This polypeptide is attached to a suitable carrier and the thus obtained product is used as vaccine. The vaccination leads to the production of antiviral antibodies (in vitro) and to the protection against infection (in vivo).

Due to its large size (~550 amino acid residues) the hemagglutinin comprises a plurality of antigenic determinants, several of which are in regions that undergo sequence changes in different strains (strain-specific determinants), and others in regions which are common for the various known hemagglutinins (common determinants). Synthetic peptides corresponding to both types of determinants can be used for the preparation of the synthetic vaccines.

Specific determinants of several influenza strains such as of the sequence

|  | Present in strain |
| --- | --- |
| Ala-Lys-Arg-Gly-Pro-Gly-Ser-Gly | (Aichi, Mem) |
| or Ala-Lys-Arg-Gly-Pro-Asp-Asn-Ser | (Texas) |
| or Ala-Lys-Arg-Gly-Pro-Asp-Asn-Gly | (Vic) |
| or Ala-Lys-Arg-Gly-Pro-Asp-Asn-Gly | (Eng/42) | and the sequences

Pro-Ser-Thr-Asp-Glu-Glu-Gln-Thr-Ser-Leu-Tyr-Val,

Phe-Phe-Ser-Arg-Leu-Asn-Trp-Leu-Tyr-Lys-Ser-Gly-Ser-Thr-Tyr-Pro-Val-Leu,

Ala-Ala-Lys-Arg-Gly-Pro-Asp-Ser-Gly-(phenylalanine)-(phenylalanine)-Ser-Arg-Leu-Asp-Tyr-Leu-Thr-Lys-Ser-Gly-Ser-Thr-Thr-Pro-Val-Leu and Ser-Lys-Ala-Phe-Ser-Asn-Ala-Tyr-Pro-Tyr-Asp-Val-Pro-Asp-Tyr-Ala-Ser-Leu which appear in the hemagglutinin of several influenza strains have now been synthesized.

All these peptides, and combinations of them, attached to macromolecular carriers are effective as synthetic vaccines. Synthetic carriers such as multi-poly-DL-alanyl-poly-L-lysine and multi-poly-L-prolyl-poly-L-lysine as well as native tetanus toxoid are suitable as carriers.

Conjugates containing peptides that form a part of the sequence of the hemagglutinin of several influenza strains produce immunity towards all such strains, with no preference, whereas the specific determinants induce immune response primarily to the particular strain with little or no cross-reactivity and immunization.

It is clear that all the sequences which are given herein are by way of example only, and that other compositions related to relevant antigenic determinants, or sequences in which limited conservative amino acid changes are introduced, can be used as well.

DESCRIPTION OF A PREFERRED EMBODIMENT

The peptide of the sequence
Ser-Lys-Ala-Phe-Ser-Asn-Ala-Tyr-Pro-Tyr-Asp-Val-Pro-Asp-Tyr-Ala-Ser-Leu
was synthesized by the solid phase peptide synthesis method of Merrifield, using the pertinent t-Boc derivatives of the various amino acids. It was purified by column chromatography, and characterized for purity by thin layer chromatography and for composition by amino acid analysis.

The peptide was attached via 1-ethyl-3-(3'-dimethylaminopropyl) carbodiimide hydrochloride (EDCI) to three different carriers:

(a) multi-poly-Dl-alanyl-poly-L-lysine (A—L); (b) multi-poly-L-prolyl-poly-L-lysine (Pro—L); and (c) purified tetanus toxoid. The three conjugates with A—L contained, respectively, 3.7, 4–5 and 7–8 moles peptide attached per mole of carrier (70,000 dalton); the conjugate with (Pro—L) contained 24 moles peptide per mole carrier (110,000 dalton) and the two conjugates with the tetanus toxoid—36.8 and 29.3 moles of peptide per mole toxoid (~150,000 dalton).

The conjugates with tetanus toxoid were used for immunization of rabbits (subcutaneous injection of 1 mg conjugate in 0.5 ml PBS emulsified with 0.5 ml complete Freund's adjuvant (CFA), followed a month later by two boosters with half the amount administered two to three weeks apart) and mice (intraperitoneal injection of 50 μg of conjugate in 0.1 ml PBS emulsified with 0.1 ml of CFA, followed a month later by one booster with half the amount). The animals were bled weekly, starting one week after the last booster. Additional boosters were given when necessary.

Figure 1:
Figure 2:
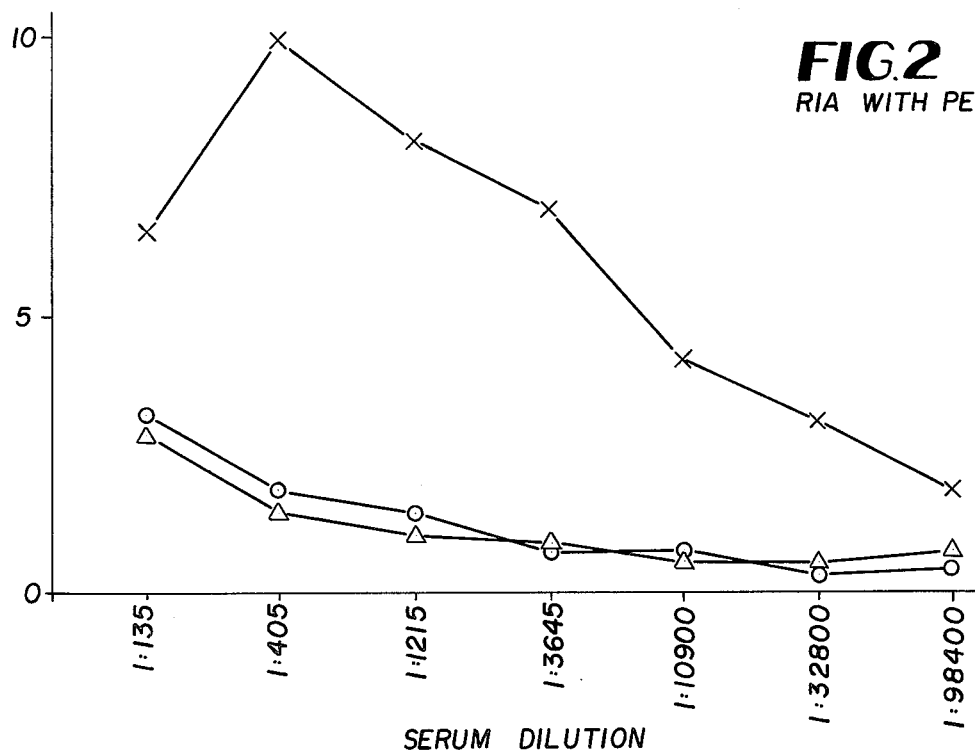
Figure 3:
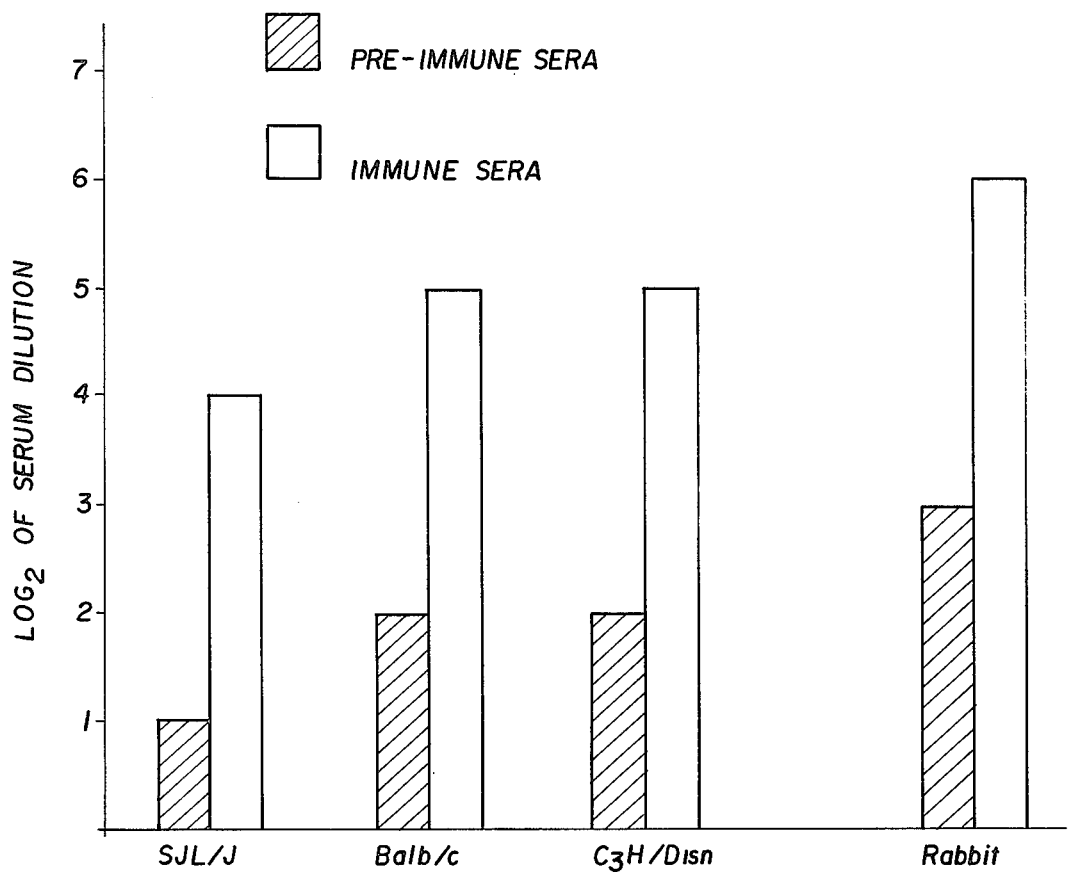

The reactivity and specificity of the rabbit antiserum was determined by several methods: (1) Double diffusion in agar gel (FIG. 1), indicating the presence of antibodies specific towards the peptide, as well as antibodies to the tetanus toxoid; (2) Solid phase radioimmunoassay in microtiter plates (FIG. 2) indicating specificity of the antibodies for the peptide and (3) Radioimmunoassay, indicating cross-reactivity of the antibodies with the intact hemagglutinins containing the above sequence.

The resultant antibodies, elicited both in rabbit and in mice of several inbred strains, are reactive with intact hemagglutinin molecule, as indicated by their capacity to inhibit the hemagglutination of chicken red blood cells (hemagglutination inhibition (HI) assay). A difference in HI titer of three $\log_2$ was observed between the immune and respective pre-immune sera (FIG. 3). This indicates that the anti-peptide specific antibodies are capable of binding to the intact hemagglutinin and of interfering with its biological function.

The rabbit antibodies against the peptide are also capable of inhibiting the infectivity of the virus, as determined in vitro in tissue culture by the plaque assay using Maden Darby Kidney Cells (MDCK) cells. As demonstrated in Table 1, up to 83% inhibition of the virus plaques is caused by the immune serum, at 1:16 dilution as compared to the effect of pre-immune serum at the same dilution. The anti-serum is effective also at a dilution of 1:32.

Immunization of mice of the inbred strain C3H/Disn with the peptide-toxoid conjugate, according to the schedule mentioned above, resulted in effective protection against infection with the Texas Influenza Virus, as indicated by reduction in virus particles in the lungs of the immunized mice (Table 2). The protective effect is demonstrated by the marked difference in the incidence of infection in the mice, as well as by the lower egg infective dose of the lung extracts of the immunized mice as compared to control groups, which were either untreated or immunized with toxoid alone prior to infection.

The synthetic vaccine illustrated above contains a peptide that is present in the hemagglutinin of at least nine different influenza strains of the subtype A and it leads to a protective effect against all of them, with no pronounced preference of one to the other.

The carrier used above, namely tetanus toxoid, is in common use in humans for vaccination against tetanus. The synthetic vaccine is thus both safe for human use, and ought to be advantageous by also providing booster immunization against tetanus together with the protection against influenza.

TABLE 1

| | Inhibition of influenza virus plaques | | | | | | |
|---|---|---|---|---|---|---|---|
| | Plaques without | Plaques with* pre-immune serum | | Plaques with* immune serum | | Inhibition* % | |
| Virus | Serum | 1:16 | 1:32 | 1:16 | 1:32 | 1:16 | 1:32 |
| $10^{-6}$ | 113 | 51.3 | 116 | 39 | 93.6 | 24 | 20 |
| $3 \times 10^{-7}$ | 47 | 27.6 | 30.6 | 6.3 | 17.6 | 83 | 17.6 |
| $10^{-7}$ | 13 | 8.6 | 17 | 3 | 5.6 | 65 | 5.6 |
| $3 \times 10^{-8}$ | 4 | 2 | 8.3 | 0 | 2.6 | — | 69 |

*All numbers represent an average of triplicate.

TABLE 2

| | Protection against infection | |
|---|---|---|
| Group | Incidence of infection[a] | EID[b] |
| Exp. 1 | | |
| Control (untreated) | | |
| Control (toxoid) | 3/4 | $10^{-4}$ |
| Vaccinated | 1/2 | $10^{-1.25}$ |
| Exp. 2 | | |
| Control (untreated) | 3/5 | $10^{-2.2}$ |
| Vaccinated | 2/10 | $10^{-0.7}$ |

[a]Number of mice per group in which virus was present in a $10^{-1}$ dilution of lung extract

[b]Egg-infective dose - lowest dilution of lung extract which still infective in eggs (average values for all the mice in each group).

We claim:

1. A synthetic vaccine against a plurality of differing influenza virus infections comprising a suitable macromolecular carrier having attached thereto a synthetic peptide corresponding to an antigenic fragment of the hemagglutinin component of an influenza virus, which antigenic fragment is common to a plurality of differing influenza virus strains and capable of eliciting antibodies capable of neutralizing each of said intact differing influenza virus strain, said antigenic fragment being selected from the group of peptides consisting of: Pro-Ser-Thr-Asp-Glu-Glu-Gln-Thr-Ser-Leu-Tyr-Val; Phe-Phe-Ser-Arg-Leu-Asn-Trp-Leu-Tyr-Lys-Ser-Gly-Ser-Thr-Tyr-Pro-Val-Leu; Ser-Lys-Ala-Phe-Ser-Asn-Ala-Tyr-Pro-Tyr-Asp-Val-Pro-Asp-Tyr-Ala-Ser-Leu; and Ala-Ala-Lys-Arg-Gly-Pro-Asp-Ser-Gly- (phenylalanine)-(phenylalanine)-Ser-Arg-Leu-Asp-Tyr-Leu-Thr-Lys-Ser-Gly-Ser-Thr-Thr-Pro-Val-Leu.

2. A synthetic vaccine in accordance with claim 1, wherein said macromolecular carrier is multi-poly-DL-alanyl-poly-L-lysine (A—L), multi-poly-L-propyl-poly-L-lysine (Pro—L), or purified tetanus toxoid.

3. A synthetic vaccine in accordance with claim 1 wherein said macromolecular carrier is purified tetanus toxoid.

4. A synthetic vaccine in accordance with claim 1, wherein said synthetic peptide is attached to said macromolecular carrier via 1-ethyl-3-(3'-dimethylaminopropyl) carbodiimide hydrochloride (EDCI).

5. A synthetic vaccine in accordance with claim 1, wherein said synthetic peptide has the structure Ser-Lys-Ala-Phe-Ser-Asn-Ala-Tyr-Pro-Tyr-Asp-Val-Pro-Asp-Tyr-Ala-Ser-Leu.

6. A synthetic vaccine in accordance with claim 5, wherein said macromolecular carrier is multi-poly-DL-alanyl-poly-L-lysine (A—L), multi-poly-L-propyl-poly-L-lysine (Pro—L), or purified tetanus toxoid.

7. A synthetic vaccine in accordance with claim 2, wherein said synthetic peptide is attached to said macromolecular carrier via 1-ethyl-3-(3'-dimethylaminopropyl) carbodiimide hydrochloride (EDCI).

8. A synthetic vaccine in accordance with claim 1 in unit dosage form.

9. A process for the vaccination of mammals against each of a plurality of differing influenza virus strains, comprising, administering to said mammal an effective quantity of a vaccine in accordance with claim 1.

10. A process for the vaccination of mammals against each of a plurality of differing influenza virus strains, comprising,
administering to said mammal an effective quantity of a vaccine in accordance with claim 2.

11. A process for the vaccination of mammals against each of a plurality of differing influenza virus strains, comprising,
administrating to said mammal an effective quantity of a vaccine in accordance with claim 5.

12. A process for the vaccination of mammals against each of a plurality of differing influenza virus strains, comprising,
administering to said mammal an effective quantity of a vaccine in accordance with claim 6.

13. A process for the vaccination of mammals against each of a plurality of differing influenza virus strains, comprising,
administering to said mammal an effective quantity of a vaccine in accordance with claim 7.

* * * * *